United States Patent [19]

Grollier

[11] Patent Number: 4,626,529
[45] Date of Patent: Dec. 2, 1986

[54] OILY COMPOSITIONS COMPRISING A DERMATOLOGICAL ACTIVE PRINCIPLE, INTENDED FOR THE TREATMENT OF THE SCALP OR SKIN

[75] Inventor: Jean F. Grollier, Paris, France

[73] Assignee: L'oreal, Paris, France

[21] Appl. No.: 673,219

[22] Filed: Nov. 20, 1984

Related U.S. Application Data

[63] Continuation of Ser. No. 436,171, Oct. 22, 1982, abandoned.

[30] Foreign Application Priority Data

Oct. 23, 1981 [LU] Luxembourg ............... 83711

[51] Int. Cl.$^4$ .................................. A61K 31/60
[52] U.S. Cl. ........................ 514/159; 514/312; 514/399; 514/439; 514/468; 514/559; 514/721; 514/732; 514/735
[58] Field of Search ............ 514/159, 312, 399, 439, 514/468, 559, 721, 732, 735

[56] References Cited

U.S. PATENT DOCUMENTS

| | | | |
|---|---|---|---|
| 3,968,218 | 7/1976 | Bouillon et al. | 424/267 |
| 4,213,960 | 7/1980 | Grollier et al. | 424/47 |
| 4,349,532 | 9/1982 | Vanlerberghe et al. | 424/47 |
| 4,367,224 | 1/1983 | Van Scott et al. | 424/175 |

FOREIGN PATENT DOCUMENTS

| | | |
|---|---|---|
| 460839 | 2/1937 | United Kingdom . |
| 776644 | 6/1957 | United Kingdom . |
| 1359226 | 9/1971 | United Kingdom . |

OTHER PUBLICATIONS

Balsam et al. "Cosmetics Science & Technology" 2nd ed. vol. 2, pp. 73–82 and 88–94, (1972).
PCT/US79/00614, "Anhydrous Multi-Purpose Moisturizing Composition", filed Aug. 14, 1979, Van Cleave.
Estrin, et al., CTFA Cosmetic Ingredient, 1982, p. 173.

Primary Examiner—Leonard Schenkman
Attorney, Agent, or Firm—Fleit, Jacobson, Cohn & Price

[57] ABSTRACT

The present invention discloses a homogeneous oily composition essentially consisting of a dermatological active principle, an oily compound and an oil-soluble surface-active component, the oil-soluble surface-active component comprising an anionic surface-active agent, the acid group of which has been neutralized by an amine, generally comprising 0.01 to 15% by weight of active principle, 5 to 85% by weight of oily compound and 15 to 95% by weight of oil-soluble surface-active agent.

15 Claims, No Drawings

OILY COMPOSITIONS COMPRISING A DERMATOLOGICAL ACTIVE PRINCIPLE, INTENDED FOR THE TREATMENT OF THE SCALP OR SKIN

This application is a continuation of application Ser. No. 436,171, filed Oct. 22, 1982, now abandoned.

DESCRIPTION

The present invention relates to new oily compositions comprising a dermatological active principle, which are intended for the treatment of the scalp and skin.

Dermatological active principles are frequently used in the form of a paste, ointment, salve, balm or emulsion. In this type of preparation, the active principle is dispersed or solubilised in a fatty phase, which is most frequently vaseline, paraffin or waxes.

However, these preparations have disadvantages both in terms of application, which is not always easy, and in terms of removal, which can be rather lengthy, and, in the case of scalp preparations, removal frequently requires rinsing with water and even shampooing.

It has now been discovered that it is possible to overcome these disadvantages by incorporating the active principle into an oily composition which can be applied as easily as an oil and which can be removed, like a shampoo, simply by adding water. This composition thus makes it possible to avoid excessively prolonged contact by the subject to active substances which can cause irritations if they are left on the skin for too long. It also makes it possible easily to remove products capable of dirtying or staining the clothes.

The present invention therefore provides a homogeneous oily composition intended for the treatment of the scalp and skin, characterised in that it essentially consists of a dermatological active principle, an oily compound and an oil-soluble surface-active component.

Preferably, the composition according to the invention contains:
 0.01 to 15% by weight of active principle,
 5 to 85% by weight of oily compound and
 15 to 95% by weight of the oil-soluble surface active component.

The oily composition according to the invention is of particular value in the case of dermatological active principles which are not sufficiently soluble in water or which are unstable in the presence of water, but which, on the other hand, are soluble in oils or alternatively in a mixture of oil and surface-active agent. Their incorporation into the oily compositions according to the invention has advantages in cosmetic treatment or in the treatment of scalp diseases, because such compositions facilitate application and, if appropriate, removal, especially when applied to the scalp.

The dermatological active principle used according to the invention is typically a member of one of the following different classes of products: anti-fungal agents, anti-bacterial agents, anti-dandruff agents, anti-seborrhea agents, anti-acne agents, keratolytic agents and anti-psoriasis agents.

Examples of anti-fungal agents which may be mentioned are econazole and miconazole.

Examples of anti-bacterial agents which may be mentioned are chlorquinol, hexachlorophene, 2,4,4'-trichloro-2'-hydroxybiphenyl ether and usnic acid.

An example of an anti-dandruff agent which may be mentioned is coal tar.

Examples of anti-seborrhea agents which may be mentioned are certain fatty substances and thioxolone.

Examples of anti-acne agents which may be mentioned are retinoic acid and its derivatives.

An example of a keratolytic agent which may be mentioned is salicyclic acid.

An example of an anti-psoriasis agent which may be mentioned is anthralin.

The oily compound may be a mineral, animal, vegetable or synthetic oil, a synthetic fatty acid triglyceride, a fatty alcohol or a fatty acid ester, used singly or in a mixture.

Vaseline oil (liquid petrolatum) may be mentioned more particularly amongst the mineral oils.

Suitable animal oils include whale oil, seal oil, menhaden oil, halibut-liver oil, cod-liver oil, tuna oil, tallow oil, bovine oil, caballine oil, ovine oil, mink oil and otter oil.

Amongst the vegetable oils, there may be mentioned almond oil, groundnut oil, wheatgerm oil, linseed oil, apricot-kernel oil, walnut oil, palm oil, pistachio oil, sesame oil, poppy oil, pine oil, castor oil, soya oil, avocado oil, safflower oil, copra oil, hazelnut oil, olive oil, grape-seed oil, sunflower oil, colza oil, cade oil, maize germ oil, peach-kernel oil, coffee-bean oil and jojoba oil.

Suitable synthetic fatty acid triglycerides include capyrlic and capric acid triglycerides and the triglycerides of fatty acids having 6 to 12 carbon atoms.

Amongst the fatty alcohols, there may be mentioned usaturated alcohols, such as oleyl alcohol, or saturated alcohols, such as 2-octyldodecanol.

Preferred fatty acid esters include the isopropyl esters of myristic, palmitic and stearic acids.

The oily compound used according to the invention can optionally be oxyethyleneated.

According to a preferred embodiment, the oily compound used comprises 30 to 100% by weight of vaseline oil and 0 to 70% by weight of vegetable oil.

The oil-soluble surface-active component is an anionic surface-active agent, the acid group of which has been neutralised so as to make it oil-soluble i.e. an amine salt is, in general, formed; a non-ionic surface-active agent and/or an alkanolamide can optionally be included.

The oil-soluble surface-active agents which are more particularly preferred according to the invention are sulphated alkanols and their unsaturated equivalents, sulphonated alkylbenzenes, carboxylated alkyl polyglycol ethers and carboxylated alkylphenol polyglycol ethers, and sulphated alkyl polyglycol ethers and sulphated alkylphenol polyglycol ethers, used singly or in a mixture and neutralised with an amine or a mixture of amines, optionally used with one or more non-ionic surface-active agents.

The sulphated alkanols which can be used are, in particular, straight-chain or branched alkanols containing from 10 to 22 carbon atoms and preferably 12 to 16 carbon atoms; the corresponding unsaturated compounds can also be used.

Amongst these alkanols, there may be mentioned, more particularly, decyl alcohol, lauryl alcohol, myristyl alcohol, cetyl alcohol, stearyl alcohol, oleyl alcohol and also alcohols obtained from oils or fats of natural origin, such as $C_{12}$–$C_{14}$ alcohols, oleyl-cetyl alcohol and $C_{12}$–$C_{18}$ fatty alcohols.

The sulphonated alkylbenzenes which are more particularly used contain a straight-chain alkyl radical having 10 to 13 carbon atoms.

Suitable sulphated alkyl polyglycol ethers include the addition products of the abovementioned alkanols with 1 to 8 mols of ethylene oxide and preferably 1.5 to 3 mols of ethylene oxide.

The sulphated alkylphenol polyglycol ethers used generally contain a straight-chain or branched alkyl radical containing from 7 to 12 carbon atoms, and 5 to 10 mols of ethylene oxide per molecule.

The carboxylated alkyl polyglycol ethers which are more particularly used contain an alkyl radical having 12 to 18 carbon atoms, and 2 to 20 mols of ethylene oxide.

The preferred carboxylated alkylphenol polyglycol ethers contain an alkyl radical having 7 to 12 carbon atoms, and 2 to 20 mols of ethylene oxide.

The amines used for the neutralisation of the acid groups of the anionic surface-active agent may be amines or alkanolamines. There may be mentioned, in particular, monoalkylamines and polyalkylamines, such as methylamine, ethylamine, diethylamine, propylamine, isopropylamine, butylamine and hexylamine, monoalkanolamines and polyalkanolamines, such as ethanolamine, diethanolamine, triethanolamine, propanolamine and mono-, di or tri-isopropanolamine, and alkylalkanolamines, such as dimethylaminoethanol, diethylaminoethanol, 2-amino-2-methylpropane-1,3-diol, 2-amino-2-methylpropanol, N,N-dimethylisopropanolamine, N-propylethanolamine, N-propyldiethanolamine, N,N-diethylaminoethoxyethanol, monobutylethanolamine, tert.-butylethanolamine and tert.-butyldiethanolamine, used singly or in a mixture.

The non-ionic surface-active agents which may be included are preferably alkyl polyglycol ethers originating from straight-chain or branched alkanols having 10 to 22 carbon atoms and preferably 10 to 16 carbon atoms, and containing 1 to 8 mols of ethylene oxide, or alkylphenol polyglycol ethers having a straight-chain or branched alkyl radical having 7 to 12 carbon atoms and oxyethyleneated with 5 to 10 mols of ethylene oxide. As oxyethyleneated alkanols which are more particularly preferred, there may be mentioned decyl, lauryl, myristyl, cetyl, stearyl and oleyl alcohols, fatty alcohols of natural origin having 12 to 14 carbon atoms, oleyl-cetyl alcohol, and fatty alcohols having 12 to 18 carbon atoms, which have been oxyethyleneated with 1 to 8 mols of ethylene oxide.

Particularly preferred surface-active components include carboxylated alkylphenol polyglycol ethers in which the alkyl radical comprises 7 to 12 carbon atoms, which contain 2 to 20 mols of ethylene oxide and which are salified by an alkanolamine and to which a non-ionic surface-active agent and an alkanolamide have been added, or a mixture composed of:

(1) 40 to 50% by weight of fatty alcohols having 10 to 18 carbon atoms and preferably 12 to 14 carbon atoms, and oxyethyleneated with 25 to 50% by weight and preferably 30 to 40% by weight of ethylene oxide;

(2) 25 to 35% by weight of sulphated oxyethyleneated fatty alcohols mentioned under (1), salified with aliphatic amines or with alkanolamines having 1 to 6 carbon atoms, more particularly isopropanolamine;

(3) 10 to 20% by weight of alkanolamides, preferably the diethanolamides of fatty acids having 10 to 18 carbon atoms; and (4) 5 to 15% by weight of sulphates or hydrochlorides of aliphatic amines or of alkanolamines having 1 to 6 carbon atoms, in particular isopropanolamine.

The fatty acid alkanolamides may be, for example, monoethanolamide, diethanolamide, propanolamide and isopropanolamide of capric acid, undecylic acid, lauric acid, myristic acid, palmitic acid, stearic acid, oleic acid as well as mixtures of fatty acids having chains containing 10 to 18 carbon atoms, such as are obtained from fats and oils of natural origin.

The amine or alkanolamine salts which can be used more particularly include ethylamine sulphate, propylamine hydrochloride, isopropylamine sulphate, butylamine sulphate, hexylamine hydrochloride, hexylamine sulphate, monoethanolamine hydrochloride, diethanolamine sulphate, triethanolamine sulphate and propanolamine hydrochloride.

The compositions which are more particularly preferred are those based on sulphated lauryl alcohol oxyethyleneated with 2 to 5 mols of ethylene oxide and neutralised, in the presence of a non-ionic surface-active agent, with an amine.

The compositions according to the invention can also contain products normally used in the treatment of the scalp and skin, such as preservatives, antioxidants and thickeners. Salicylic acid may be mentioned as preservative.

According to one embodiment of the invention, the homogeneous oily composition is prepared just at the time of use, by mixing a first composition containing the dermatological active principle solubilised in the oily compound, with a second composition containing the oil-soluble surface-active agent, in the presence of an oily compound, it being possible for this second oily compound to be different from the first.

The compositions are applied to the scalp or skin. After an application time of, say, 5 to 30 minutes, they are emulsified and rinsed off.

The compositions according to the invention can be used as a shampoo or as a rinse.

When used as a shampoo, the product may be applied to dirty hair, which is preferably dry.

After an application time of at least 5 minutes, the product is emulsified and then rinsed off. The composition can be applied again for a second shampooing. An amount of the order of 30 to 40 ml of the composition according to the invention is typically used for this purpose.

When used as a rinse, the product is applied, left for at least 5 minutes and then rinsed off. An amount of the order of 15 to 30 ml of the composition according to the invention, and preferably 15 to 25 ml, is suitably used in this case.

The following Examples further illustrate the present invention.

EXAMPLE 1

(Shampoo)

The following anti-psoriasis composition is prepared:

| | |
|---|---|
| Anthralin | 0.1 g |
| The monoisopropanolamine salt of sulphated oxyethyleneated lauryl alcohol containing 85% of active ingredient in ethanol | 35 g |

-continued

| | |
|---|---|
| Isopropyl myristate q.s. | 100 g |

This composition is applied to the scalp of dry dirty hair.

After an application time of 15 minutes, the composition is emulsified and then rinsed off.

EXAMPLE 2

(Shampoo)

The following bactericidal composition is prepared:

| | |
|---|---|
| 2,4,4'-Trichloro-2'-hydroxybiphenyl ether sold by CIBA-GEIGY under the name IRGASAN DP 300 | 1 g |
| Surface-active agent composed of the monoisopropanolamine salt of sulphated oxyethyleneated lauryl alcohol and of a nonionic, sold by ZSCHIMMER & SCHWARZ under the name ZETESOL 100 | 35 g |
| Vaseline oil | 25 g |
| Jojoba oil q.s. | 100 g |

This composition is applied as described in Example 1.

EXAMPLE 3

(Shampoo)

The following anti-dandruff composition is prepared:

| | |
|---|---|
| Distilled coal tar sold by RUTGERSWERRE under the name FLUXOL ST | 10 g |
| Surface-active agent composed of the monoisopropanolamine salt of sulphated oxyethyleneated lauryl alcohol, of a non-ionic and of copra diethanolamide, sold by HENKEL under the name TEXAPON WW 99 | 30 g |
| Vaseline oil | 21 g |
| Colza oil q.s. | 100 g |

This composition is applied to the roots and scalp of dry dirty hair.

After an application time of 25 minutes, the composition is emulsified and rinsed off. After rinsing, the composition is applied to the scalp and hair again in order to carry out a second shampooing, and it is left for 5 minutes and then rinsed off.

EXAMPLE 4

The following anti-psoriasis composition is prepared:

| | |
|---|---|
| Anthralin | 0.05 g |
| The monoisopropanolamine salt of the acid of the formula: R-O[CH$_2$—CH$_2$—O]$_n$CH$_2$COOH, in which R = octylphenyl and n = 4 | 10 g |
| C$_{12}$-C$_{14}$ fatty alcohols oxyethyleneated with 2 to 3 mols of ethylene oxide | 5 g |
| Copra diethanolamide | 5 g |
| Isopropyl myristate q.s. | 100 g |

This composition is applied to the skin or to the scalp of dry dirty hair. After an application time of 10 minutes, the composition is emulsified and rinsed off. The application of the composition is followed by shampooing in order to wash the hair during the treatment of the scalp.

EXAMPLE 5

1 part of composition (1) is mixed at the time of use with 3 parts of composition (2).

Composition (1):

| | |
|---|---|
| Anthralin | 0.4 g |
| Salicylic acid | 0.25 g |
| Isopropyl myristate q.s. | 100 g |

Composition (2):

Surface-active agent composed of the monoisopropanolamine salt of sulphated oxyethyleneated lauryl alcohol, of a nonionic and of copra diethanolamide, sold by HENKEL under the name

| | |
|---|---|
| TEXAPON WW 99 | 46.7 g |
| Isopropyl myristate q.s. | 100 g |

In this example, the isopropyl myristate in composition (1) can be replaced by isopropyl palmitate.

The isopropyl myristate in composition (2) can be replaced by the following mixture:

| | |
|---|---|
| Vaseline oil | 21.3 g |
| Groundnut oil | 32 g |

The composition obtained is applied as described in Example 1.

EXAMPLE 6

1 part of composition (1) is mixed at the time of use with 3 parts of composition (2).

Composition (1):

| | |
|---|---|
| Anthralin | 0.4 g |
| Isopropyl myristate q.s | 100 g |

Composition (2):

The triisopropanolamine salt of the surface-active agent of the formula:

| | |
|---|---|
| RO(CH$_2$CH$_2$—O)$_n$CH$_2$—COOH, in which R = octylphenyl and n = 4 | 23.3 g |
| Oxyethyleneated fatty alcohols (C$_{12}$-C$_{14}$ alcohols containing 2 to 3 mols of ethylene oxide) | 11.7 g |
| Copra diethanolamide | 11.7 g |
| Isopropyl myristate q.s. | 100 g |

The composition obtained is applied as described in Example 1.

EXAMPLE 7

The following anti-seborrhea composition is prepared:

| | |
|---|---|
| Thioxolone | 4 g |
| Texapon WW 99 | 35 g |
| Vaseline oil | 25 g |
| Groundnut oil | 36 g |

It is applied to the scalp, left for 10 minutes and then emulsified and rinsed off.

EXAMPLE 8

The following keratolytic composition is prepared:

| | |
|---|---|
| Salicylic acid | 0.5 g |
| Texapon WW 99 | 35 g |
| Isopropyl myristate | 64.5 g |

This composition is applied to the skin in order to remove the dead cells. It is left for 15 minutes and then emulsified and rinsed off.

EXAMPLE 9

The following bactericidal composition is prepared:

| | |
|---|---|
| Crystalline d-usnic acid | 2 g |
| Texapon WW 99 | 35 g |
| Vaseline oil | 25 g |
| Groundnut oil | 38 g |

This composition is applied to the scalp, left for 20 minutes and then emulsified and rinsed off.

I claim:

1. A homogeneous oily composition which is substantially free of water and suitable for the treatment of the scalp and/or skin, which consists essentially of 0.01 to 15% by weight of a dermatological active principle which is substantially insoluble in water or unstable in the presence of water, 5 to 85% by weight of an oily compound and 15 to 95% by weight of an oil-soluble surface-active component comprising an anionic surface-active agent, the acid group of which has been neutralised by an amine.

2. A composition according to claim 1 in which the dermatological active principle is an anti-fungal agent, an anti-bacterial agent, an anti-dandruff agent, an anti-seborrhea agent, an anti-acne agent, a keratolytic agent or an anti-psoriasis agent.

3. A composition according to claim 2 in which the anti-fungal agent is econazole or miconazole, the anti-bacterial agent is chlorquinol, hexachlorophene, 2,4,4'-trichloro-2'-hydroxybiphenyl ether or usnic acid, the anti-seborrhea agent is a fatty substance or thioxolone, the anti-acne agent is retinoic acid or a derivative thereof, the keratolytic agent is salicylic acid, the anti-psoriasis agent is anthralin and the anti-dandruff agent is coal tar.

4. A composition according to claim 1, in which the oily compound is a mineral oil, animal oil, vegetable oil, synthetic oil, synthetic fatty acid triglyceride, fatty alcohol or fatty acid ester.

5. A composition according to claim 4 in which the mineral oil is liquid petrolatum, the animal oil is whale oil, seal oil, menhaden oil, halibut-liver oil, cod-liver oil, tuna oil, tallow oil, bovine oil, caballine oil, ovine oil, mink oil or otter oil, the vegetable oil is almond oil, groundnut oil, wheatgerm oil, linseed oil, apricot-kernel oil, walnut oil, palm oil, pistachio oil, sesame oil, poppy oil, pine oil, castor oil, soya oil, avocado oil, safflower oil, copra oil, hazelnut oil, olive oil, grape-seed oil, sunflower oil, colza oil, cade oil, maize germ oil, peach-kernel oil, coffee-bean oil or jojoba oil, the synthetic fatty acid triglyceride is a caprylic and capric acid triglyceride or a triglyceride of a fatty acid having 6 to 12 carbon atoms, the fatty alcohol is oleyl alcohol, or 2-octyldodecanol, and the fatty acid ester is an isopropyl ester of myrstic, palmitic or stearic acid.

6. A composition according to claim 4 in which the oily compound comprises 30 to 100% by weight of liquid petrolatum and 0 to 70% by weight of vegetable oil.

7. A composition according to claim 1, in which the oil-soluble surface-active component comprises a non-ionic surface-active agent and/or an alkanolamide.

8. A composition according to claim 1 in which the anionic surface-active agent is a sulphated alkanol, sulphonated alkylbenzene, sulphated or carboxylated alkyl polyglycol ether or a sulphated or carboxylated alkylphenol polyglycol ether.

9. A composition according to claim 7 in which the non-ionic surface-active agent is an alkyl polyglycol ether or alkylphenol polyglycol ether.

10. A composition according to claim 7 in which the oil-soluble surface-active component consists of:
(1) 40 to 50% by weight of a fatty alcohol having 10 to 18 carbon atoms and oxyethyleneated with 25 to 50% by weight of ethylene oxide,
(2) 25 to 35% by weight of oxyethyleneated fatty alcohol as defined under (1) which has been sulphated and salified with an aliphatic amine or alkanolamine,
(3) 10 to 20% by weight of alkanolamide and
(4) 5 to 15% by weight of sulphate or hydrochloride of an aliphatic amine or alkanolamine.

11. A composition according to claim 7 in which the oil-soluble surface-active component is a carboxylated alkylphenol polyglycol ether in which the alkyl radical comprises 7 to 12 carbon atoms, which contains 2 to 20 mols of ethylene oxide and which has been salified by an alkanolamine, together with a non-ionic surface-active agent and an alkanolamide.

12. A composition according to claim 1 which contains one or more preservative, antioxidant or thickener.

13. A homogeneous oily composition suitable for the treatment of the scalp and/or skin which consists essentially of 0.01 to 15% by weight of a dermatological active principle selected from the group consisting of econazole, miconazole, chlorquinol, hexachlorophene, 2,4,4'-trichloro-2'-hydroxybiphenyl ether, usnic acid, thioxolone, retinoic acid or a derivative thereof, salicylic acid, anthralin and coal tar, 5 to 85% by weight of an oily compound selected from the group consisting of mineral oils, animal oils, vegetable oils, synthetic oils, synthetic fatty acid triglycerides, fatty alcohols and fatty acid esters and 15 to 95% by weight of an oil-soluble surface-active component comprising an anionic surface-active agent selected from the group consisting of sulphated alkanols, sulphonated alkylbenzenes, sulphated or carboxylated alkyl polyglycol ethers and sulphated or carboxylated alkylphenol polyglycol ethers, the acid group of which has been neutralised by an amine.

14. A homogeneous oily composition which is substantially free of water and suitable for the treatment of the scalp and/or skin, which consists essentially of 0.01 to 15% by weight of a dermatological active principle which is substantially insoluble in water or unstable in the presence of water; 5 to 85% by weight of an oily compound; and 15 to 95% by weight of an oil-soluble surface-active component comprising an anionic surface-active agent, the acid group of which has been neutralized by at least one amine selected from the group consisting of methylamine, ethylamine, diethylamine, propylamine, isopropylamine, butylamine, hexylamine, ethanolamine, diethanolamine, triethanolamine, propanolamine, mono-, di- or tri-isopropanolamine, dimethylaminoethanol, diethylaminoethanol, 2-amino-2-methylpropane-1,3-diol, 2-amino-2-methylpropanol, N,N-dimethylisopropanolamine, N-propylethanolamine, N-propyldiethanolamine, N,N-diethylaminoethoxyethanol, monobutylethanolamine, tert.-butylethanolamine, and tert.-butyldiethanolamine.

15. A method of treating the skin or the scalp which comprises applying thereto an effective amount of a homogeneous oily composition as defined in claim 1, leaving said composition in contact with the skin or the scalp for a period of from 5 to 30 minutes, emulsifying and rinsing off.

* * * * *